US012496070B2

(12) United States Patent
Clause et al.

(10) Patent No.: US 12,496,070 B2
(45) Date of Patent: Dec. 16, 2025

(54) RETRACTABLE CUTTING GUIDE

(71) Applicant: GANYMED ROBOTICS, Paris (FR)

(72) Inventors: Thomas Clause, Paris (FR); Samuel El Guedj, Genneville (FR); Blaise Bleunven, Paris (FR)

(73) Assignee: GANYMED ROBOTICS, Paris (FR)

( * ) Notice: Subject to any disclaimer, the term of this patent is extended or adjusted under 35 U.S.C. 154(b) by 261 days.

(21) Appl. No.: 18/007,331

(22) PCT Filed: Jul. 30, 2021

(86) PCT No.: PCT/EP2021/071495
§ 371 (c)(1),
(2) Date: Jan. 30, 2023

(87) PCT Pub. No.: WO2022/023568
PCT Pub. Date: Feb. 3, 2022

(65) Prior Publication Data

US 2023/0293187 A1 Sep. 21, 2023

(30) Foreign Application Priority Data

Jul. 31, 2020 (EP) .................................... 20305884

(51) Int. Cl.
*A61B 17/15* (2006.01)
*A61B 17/14* (2006.01)

(52) U.S. Cl.
CPC ............ *A61B 17/15* (2013.01); *A61B 17/142* (2016.11)

(58) Field of Classification Search
CPC .............................. A61B 17/15; A61B 17/142
See application file for complete search history.

(56) References Cited

U.S. PATENT DOCUMENTS 5,817,097 A * 10/1998 Howard ............. A61B 17/1764 606/88
8,894,654 B2 * 11/2014 Anderson ............. B25B 21/002 173/176

(Continued)

FOREIGN PATENT DOCUMENTS

DE 102016105208 B3 7/2017
EP 0415837 A2 3/1991

(Continued)

OTHER PUBLICATIONS

International Search Report, issued on Oct. 18, 2021, in corresponding International Patent Application No. PCT/EP2021/071495, 4 pages.

(Continued)

*Primary Examiner* — Andrew Yang
(74) *Attorney, Agent, or Firm* — Morgan, Lewis & Bockius LLP

(57) ABSTRACT

A cutting guide aimed at being connected to a surgical cutting tool, including: a casing, a cutting blade, a sliding mechanism connected to the casing, a sliding unit coupled to the casing via the sliding mechanism, the sliding unit further cooperates by sliding with the sliding mechanism, a blade maintaining element carried by the sliding unit, being designed to cooperate with the cutting blade in order to maintain the blade aligned with the sliding axis, an abutment element carried by the sliding unit, being aimed at abutting against an abutment body part. The sliding mechanism and the sliding unit are configured to be positioned below the cutting blade in use configuration, and the sliding unit, the blade maintaining element and the abutment element remain static with regards to an anatomical element when the cutting guide is activated.

24 Claims, 5 Drawing Sheets

(56) References Cited

U.S. PATENT DOCUMENTS

| | | | | |
|---|---|---|---|---|
| 2005/0171545 | A1* | 8/2005 | Walsh .................. | A61B 17/154 606/88 |
| 2015/0039037 | A1 | 2/2015 | Donner et al. | |
| 2019/0083191 | A1 | 3/2019 | Gilhooley et al. | |

FOREIGN PATENT DOCUMENTS

| | | | |
|---|---|---|---|
| JP | 2005-534420 | A | 11/2005 |
| JP | 2014-504173 | A | 2/2014 |
| WO | 9325157 | A1 | 12/1993 |
| WO | 2004/012607 | A2 | 2/2004 |
| WO | 2012/068113 | A1 | 5/2012 |

OTHER PUBLICATIONS

Official Action for related Japanese Patent Application No. 2023-506178, mailed Dec. 24, 2024 (with English translation).

* cited by examiner

RETRACTABLE CUTTING GUIDE

FIELD

The present invention relates to the field of surgical cutting tools, more precisely to the field of surgical cutting guides.

BACKGROUND

When cutting a patient's bone, in particular during the bone preparation phase of a joint replacement surgery, such as, for instance, a total knee arthroplasty, a surgeon uses a well-known surgical cutting tool, usually a sagittal saw. Such a tool includes an oscillating blade which oscillates within a plane P known as the cutting plane P. During the cutting operation, the surgeon may apply a certain force/pressure on the tool. Under this pressure, the blade, due to its thinness, tends to buckle (bend) when touching the bone, causing the blade to deviate from the original cutting plane. The aim of the current invention is to reduce this bending effect in order to keep the blade as close as possible to the cutting plane P.

In order to do so, the current application is about a retractable cutting guide.

A cutting guide for the saw blade may be employed to reduce buckling as the cutting guide is configured to hold the saw blade in place while making the necessary cuts. The use of cutting guides often require the use of longer blades, which can still introduce skiving effects. Additionally, most of the currently used cutting guides requires that the cutting guide is first secured to the bone at the desired location so that the surgery time is increased. Furthermore, the actually available cutting guide are bulky, cluttering the field of view of the surgeon and bothering the surgeon during the cutting operation Finally, some cutting tool uses cutting guides being monitored by means of active control systems, said control systems being part of a robotic cutting system.

This active control system may deprive the surgeon of their freedom of movement, and iterative corrections of the control system may induce some lagging, thus decreasing both the maneuverability and precision of the cutting operation. Furthermore, an active control system requires an expensive automation equipment regarding to the function of guiding the cutting blade. Also, the system described partially hides the blade, thereby reducing the operator's field of view.

In robotic surgery, one of the goals is to increase cutting accuracy and reduce cutting time, which can be difficult in cases where the saw blade is unable to initially cut at a desired location and the surgeon does not have a clear view of the saw and the bone at the same time.

The current application aims at overcome those drawbacks.

SUMMARY

In order to overcome those drawbacks, the current invention thus relates to surgical cutting tool, such as an oscillating saw, comprising:

- a cutting blade aimed at cutting an anatomical element of a patient according to a cutting plane,
- a casing enclosing a motor, said motor being connected to said cutting blade, and
- a cutting guide comprising:
- a sliding mechanism connected to the casing,

- a sliding unit coupled to the casing by means of the sliding mechanism, the sliding unit defining a sliding axis being sensibly parallel with the cutting plane, and cooperates by sliding with the sliding mechanism, the sliding unit being aimed at sliding along the casing,
- a blade maintaining element carried by the sliding unit, the blade maintaining element being configured to cooperate with the cutting blade in order to maintain the cutting blade aligned with the sliding axis,
- an abutment element carried by the sliding unit, said abutment element being aimed at abutting against an abutment body part of the patient, wherein the sliding mechanism and the sliding unit are configured to be positioned below the cutting blade in use configuration, and wherein the sliding unit, the blade maintaining element and the abutment element remain static with regards to the patient's anatomical element when the cutting guide is activated by the pressure resulting from the surgical cutting tool being pushed towards said patient's anatomical element.

When the surgical cutting tool is held by the surgeon for performing a cut (i.e., use configuration), the sliding mechanism and the sliding unit are advantageously positioned beneath the cutting blade so that the whole blade is visible to the surgeon during the cutting operation. Therefore, in the present invention the smart positioning of the sliding mechanism and the sliding unit of the cutting guide allows to avoid the undesirable skiving (e.g., deviation from an intended cut plane and/or deviation from an intended entry point) that occurs during the cutting process while gathering the whole cutting blade in full sight of the surgeon.

According to one embodiment, the abutment element is configured to be positioned below the cutting blade in use configuration.

According to one embodiment, also the blade maintaining element is configured to be positioned entirely below the cutting blade in use configuration. In this configuration, all the elements of the cutting guide positioned entirely below the cutting blade in use configuration, which provides an even more free field of view for the surgeon, all without losing precision due to the undesired skiving. Indeed, even in this configuration the blade is advantageously supported by the blade maintaining element.

According to one embodiment, the sliding mechanism is a passive mechanism. This embodiment advantageously allows to prevent the risk of lagging and the risk of electronical breakdown. Being free of any sort of complicated electronic device, the surgical cutting tool according to the present invention is light, easy to handle and does not reduce the fluidity of the cutting operation.

The surgical cutting tool according to the invention may include one or several of the following features presented in the following embodiments, taken isolated from each other or in combination which each other.

According to one embodiment, the cutting blade displays a front and a back end, the front end being the cutting end and the back end being the end connected to the casing.

According to one embodiment, the cutting guide displaying two configurations:

- a resting configuration in which the blade maintaining element cooperates with the cutting blade nearby the front end of the blade,
- an active configuration in which the blade maintaining element cooperates with the cutting blade nearby the back end of the blade, wherein the cutting guide changes from the resting configuration to the active configuration when the cutting guide is activated.

According to one embodiment, when sliding mechanism is a passive mechanism, it includes at least one spring element being configured to cooperate with the sliding unit in order to enable the cutting guide to change from the active configuration to the resting configuration when the cutting guide stops being activated.

According to one embodiment, the blade maintaining element comprises a magnet aimed at cooperating by magnetization with the cutting blade.

According to one embodiment, the blade maintaining element comprises a slot aimed at receiving the cutting blade.

According to one embodiment, the blade maintaining element at being positioned under the cutting blade.

According to one embodiment, the abutment element is configured to block the cutting guide along an axis sensibly perpendicular to the sliding axis.

According to one embodiment, the abutment element displays at least one spike aimed at reversibly securing the cutting guide to an abutment body part of the patient.

According to one embodiment, the abutment element displays at least one transversal ridge aimed at reversibly securing the cutting guide to an abutment body part of the patient along the direction of the axis sensibly perpendicular to the sliding axis.

According to one embodiment, the abutment element displays a rounded shape aimed at fitting a natural curve of an abutment body part of the patient, According to one embodiment, the abutment element displays an ergonomic shape configured to allow a comfortable and safe positioning of the operator's hand, According to one embodiment, the cutting guide is integrally formed with the casing, According to one embodiment, the invention relates to a cutting guide aimed at being connected to a surgical cutting tool such as an oscillating saw, said tool comprising a casing enclosing a motor, said motor being connected to the cutting blade, a cutting blade aimed at cutting a patient's anatomical element according to a cutting plane. The cutting guide comprises:

- a sliding mechanism connected to the casing,
- a sliding unit coupled to the casing by means of the sliding mechanism, the sliding unit being aimed at sliding along the casing, the sliding unit defining a sliding axis being sensibly parallel with the cutting plane, the sliding unit further cooperates by sliding with the sliding mechanism,
- a blade maintaining element carried by the sliding unit, the blade maintaining element being designed to cooperate with the cutting blade in order to maintain the blade aligned with the sliding axis,
- an abutment element carried by the sliding unit; the abutment element being aimed at abutting against an abutment body part of the patient.

The sliding mechanism is a passive mechanism, and the sliding unit, the blade maintaining element and the abutment element remain static with regards to the patient's anatomical element when the cutting guide is activated by the pressure resulting from the cutting tool being pushed towards said patient's anatomical element.

As the cutting guide according to the present invention relies on a passive mechanism, there is no risk of lagging and no risk of any electronical breakdown. Being free of any sort of complicated electronic device, the cutting guide according to the present invention is light, easy to handle and does not reduce the fluidity of the cutting operation.

DETAILED DESCRIPTION

Figure 1:
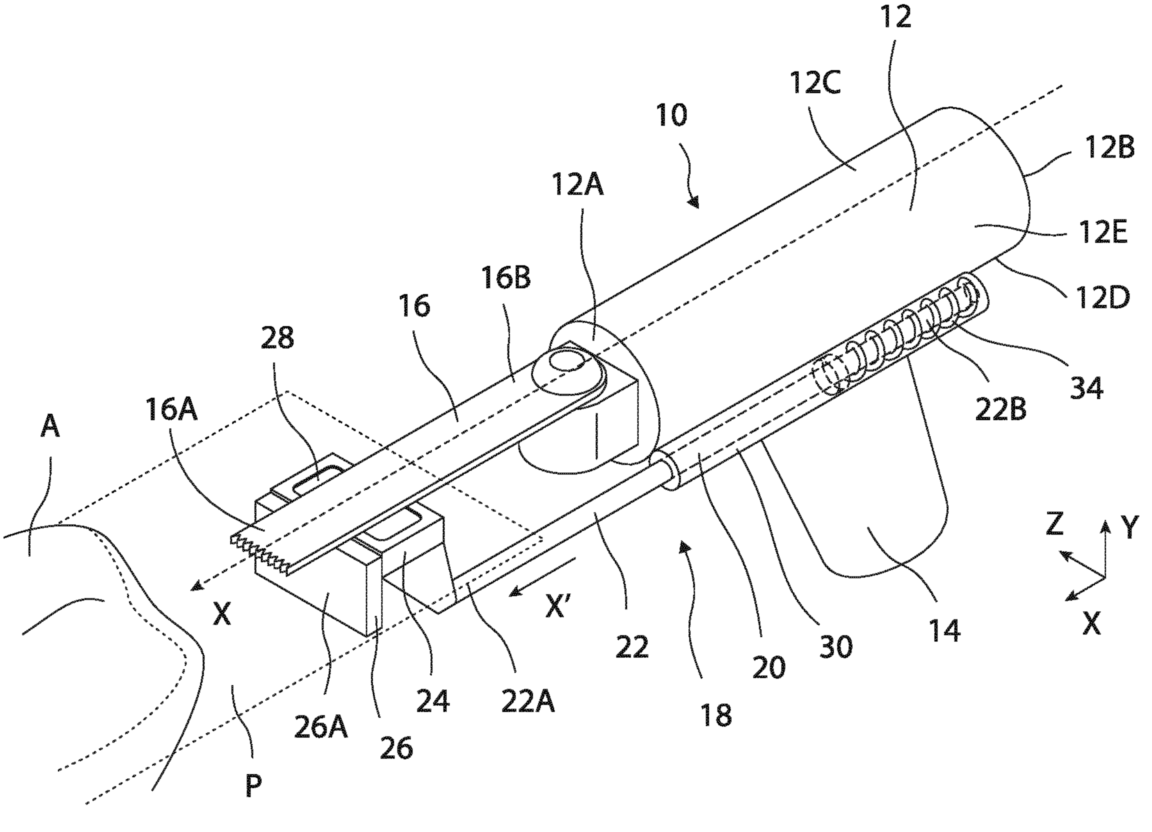
FIG. 1 is a perspective view of a surgical cutting tool equipped with a first embodiment of the cutting guide according to the present invention.
Figure 10:
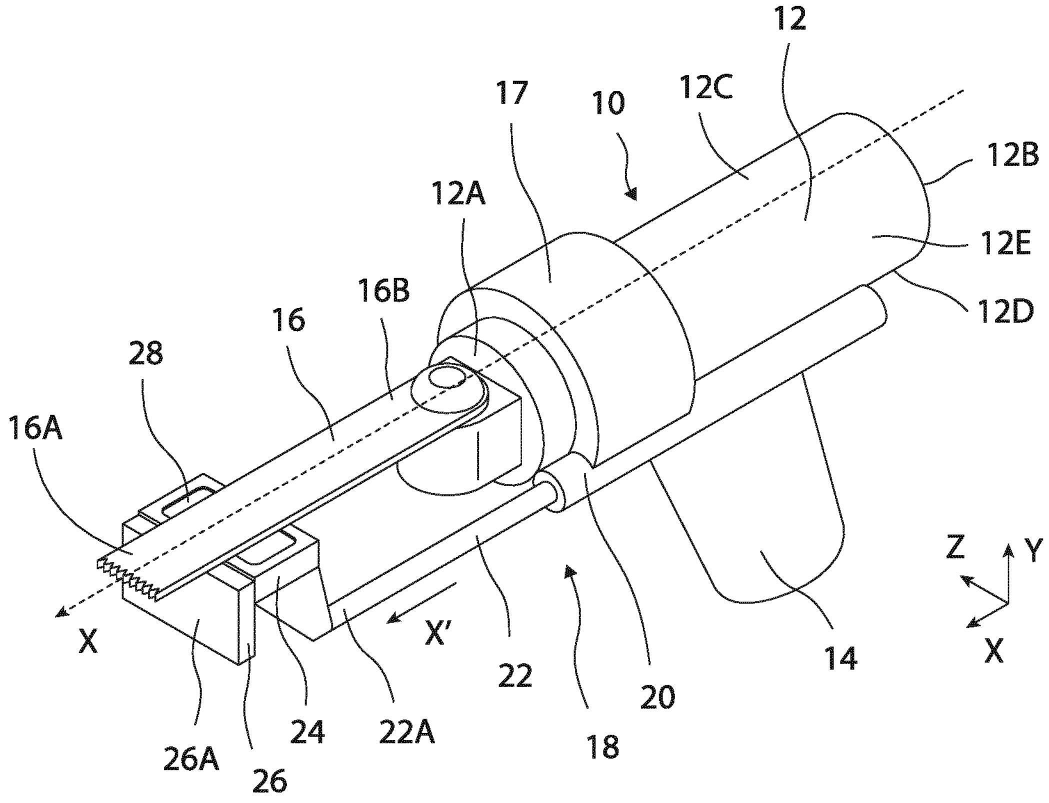
FIG. 10 is a perspective view of a surgical cutting tool equipped with a third embodiment of the cutting guide according to the present invention.

As can be seen on FIGS. 1 and 10, a surgical cutting tool 10 displays a general elongated shape extending along an elongation axis X, defining a cutting direction. The surgical cutting tool 10 comprises a casing 12 extending along said elongation axis X. The casing 12 encloses a motor (not represented) aimed at putting the surgical tool 10 into motion. The casing 12 displays a front face 12A, a back face 12B linked to each other by, according to an axis Y sensibly perpendicular to the elongation axis X, an upper face 12C, an underside face 12D and, according to a transversal axis Z, two flank sides 12E. On the example illustrated on FIGS. 1, 2, 3 and 10, the casing 12 displays a cylindrical shape of approximately 150 mm long and 40 mm wide. The surgical cutting tool 10 aims at being handled by an operator, in particular a surgeon, by means of a handle 14 connected to the casing 12. In the example illustrated on FIGS. 1, 2, 3 and 10 the handle 14 extends, from the underside 12D. In this case, when the surgical cutting tool 10 is used by the operator (i.e., in use configuration), the underside 12D is out of their field of vision.

In the current application, the terminology "sensibly" refers to the measurement error margin.

In the current application, the terminologies "front" and "back" of the various elements take are defined with regards to the cutting direction, the front being oriented positively along the cutting direction and the back being orientated negatively along the cutting direction.

The surgical tool 10 further comprises a cutting blade 16. This cutting blade 16 is aimed at cutting a patient's anatomical element A, for example a bone. This cut takes place, as already mentioned in the introduction, within a cutting plane P. The cutting blade 16 displays two ends: a front end 16A and a back end 16B. The front end 16A is the end aimed at cutting the anatomical element A, it is the cutting end. The back end 16B is the end which is connected to the motor inside the casing 12 and thus connected to the casing 12. In a well-known way, the cutting blade 16 oscillates within the plane P around a rotation axis sensibly parallel to the Y axis situated nearby the font face 12A of the casing 12. The angular rotation of the cutting blade 16 is around 4 degrees. In the examples of FIGS. 1, 2, 3 and 10, the cutting blade is made of a bio-compatible stainless steel and is about 110 mm long.

According to the present invention, in order to prevent the cutting blade 16 from bending during a cutting operation, the surgical tool 10 displays a cutting guide 18. This cutting guide 18 may be a separate piece that can be attached to and detached from the casing 12.

In the embodiment illustrated on FIG. 10, the cutting guide 18 is attached to the surgical tool 10 by means of a clamping system 17. The cutting guide 18 may also be integrally formed with, or integrated within the casing 12 as illustrated on FIGS. 1, 2 and 3.

According to the current invention, the cutting guide 18 comprises:

a sliding mechanism 20 connected to the casing 12, a sliding unit 22 coupled to the casing 12 by means of the sliding mechanism 20, a blade maintaining element 24 carried by the sliding unit 22, an abutment element 26 carried by the sliding unit 22.

Figure 2:
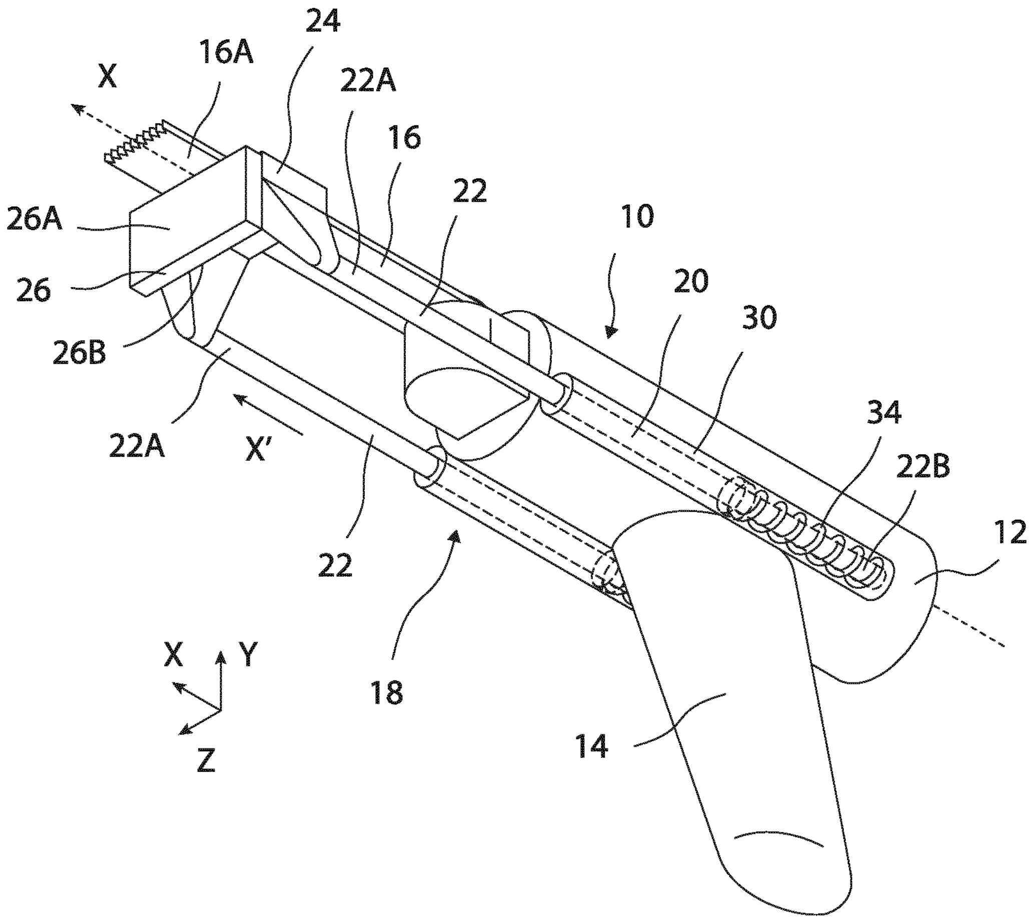
FIG. 2 is an underneath view of the surgical cutting tool equipped with the same embodiment of the cutting guide according to the present invention.
Figure 3:
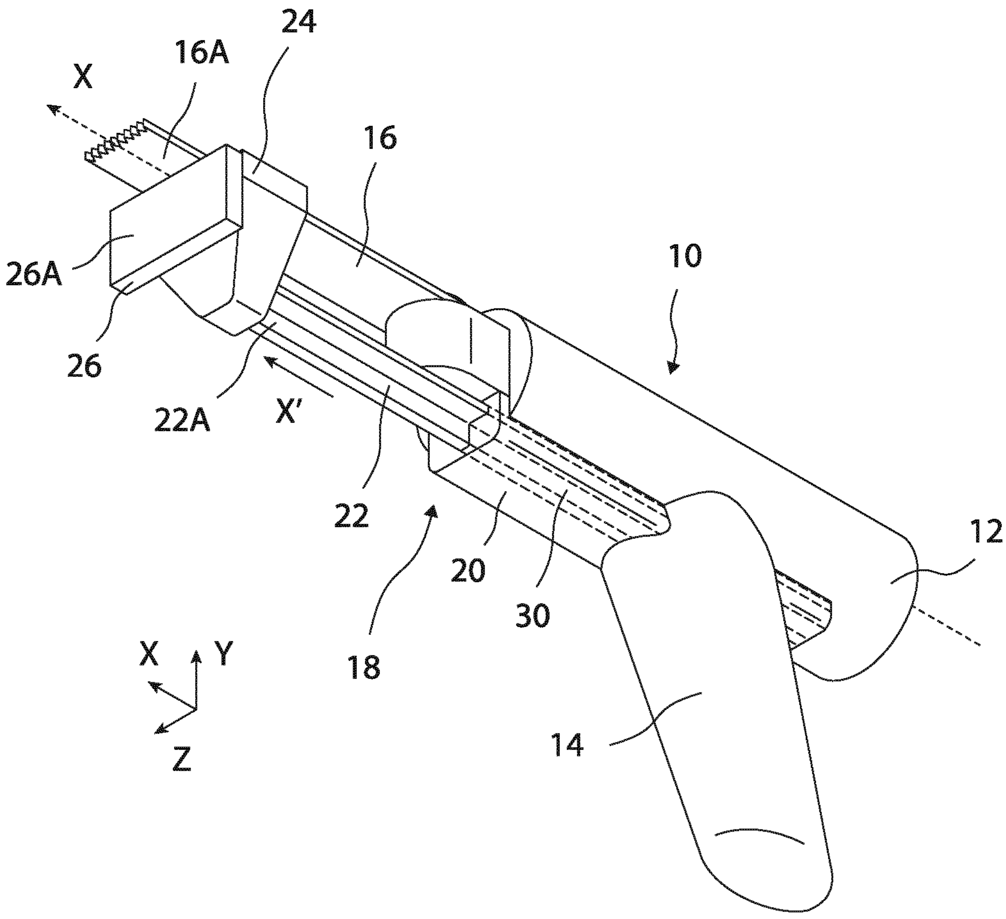
FIG. 3 is an underneath view of the surgical cutting tool equipped with a second embodiment of the cutting guide according to the present invention.

The sliding unit 22 is aimed at sliding along the casing 12. The sliding unit 22 thus defines a sliding axis X' which, in the embodiments illustrated on FIGS. 1, 2 and 3 is sensibly aligned with the elongation axis X of the surgical tool 10. The sliding axis X' is further sensibly parallel with the cutting plane P. The sliding unit 22 displays a front end 22A and a back end 22B. The back end 22B of the sliding unit 22 cooperates with the sliding mechanism 20. More precisely, as illustrated on FIGS. 1, 2 and 3, the sliding unit 22 moves through the sliding mechanism 20.

In the embodiment illustrated on FIGS. 1 and 2, the sliding unit 22 comprises at least one sliding rod, in particular two sliding rods. Each sliding rod extends, parallel to the sliding axis X', along one flank side 12E of the casing 12. The presence of two sliding rods leads to an increase in stability and balance during operation. In the embodiment illustrated on FIG. 3, the sliding unit 22 comprises a single sliding rod.

Figure 4:
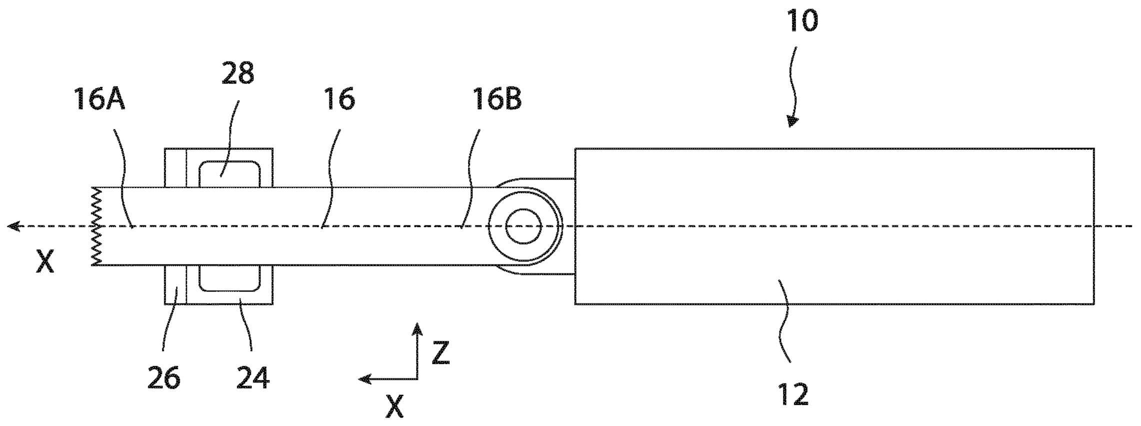
FIG. 4 is a top view of the surgical tool equipped with the second embodiment of the cutting guide according to the present invention.

In this embodiment, the sliding rod displays a general T shape. This T shape allows the rod to remain compact while displaying an improved stiffness, and further prevent the sliding rod from rotating around the axis X'. The single rod extends along the underside 12D of the casing 12 and is thus, during operation, invisible to the operator, as can be grasped from FIG. 4.

As already mentioned, the sliding unit 22 carries a blade maintaining element 24 and an abutment element 26. More precisely, and as can be seen on FIGS. 1, 2 and 3, the blade maintaining element 24 and the abutment element 26 are carried by the front end 22A of the sliding unit 22.

The blade maintaining element 24 is designed to cooperate with the cutting blade 16 in order to maintain the cutting blade 16 aligned with the sliding axis X'. During operation, the cooperation between the cutting blade 16 and the maintaining element 24 leads the cutting blade 16 to remain aligned within the cutting plane P. More precisely, the blade maintaining element 24 is positioned in such a way that, when the cutting guide 18 and the cutting blade 16 are both attached to the casing 12, the cutting blade 16 is in contact with the maintaining element 24. The blade maintaining element 24 thus aims at aligning the cutting blade 16 with the sliding unit 22, thus guiding the cutting blade 16 during the cutting operation. During operation, the forces applied on the axis Y are thus supported by the sliding unit 22, preventing the blade from bending.

Figure 9:
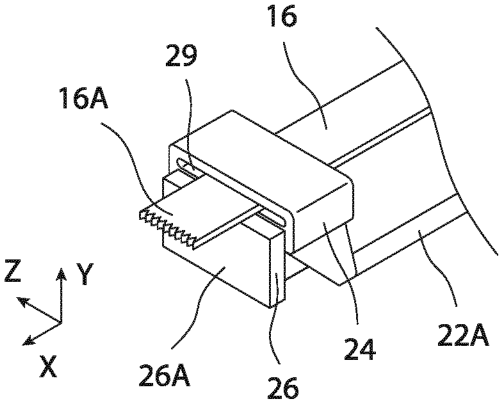
FIG. 9 is a detailed perspective view of an alternative embodiment of a maintaining element according to the present invention.

In the embodiments illustrated on FIGS. 1, 2 and 3, the blade maintaining element 24 displays a rectangular shape and comprises, on its upper face, a magnet 28 aimed at cooperating by magnetisation with the cutting blade 16. In this embodiment, the upper face (according to axis Y) of the blade maintaining element 24 cooperates with an underside face (according to axis Y) of the cutting blade 16. More precisely, the magnet 28 aims at holding the cutting blade 16 by magnetization. In the specific case of the embodiment illustrated on FIG. 1, the magnet 28 is situated inside a recess, preventing the cutting blade 16 to rub over the magnet 28 and its resulting abrasion. In an alternative embodiment illustrated on FIG. 9, the blade maintaining element 24 comprises a slot 29 aimed at receiving the cutting blade 16.

In one advantageous embodiment, in order to ease the use of the surgical cutting tool 10, the blade maintaining element 24 is preferably positioned under (according to the Y axis) the cutting blade 16. This way, the blade maintaining element 24 is outside the operator's field of view and does not disturb the cutting operation.

Figure 5:
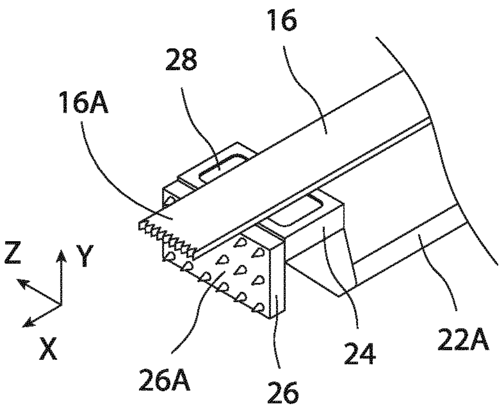
FIGS. 5, 6 7 and 8 are four detailed perspective views of four different embodiments of an abutment element according to the present invention.
Figure 6:
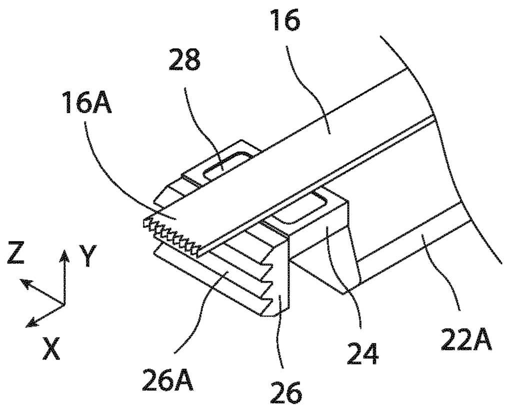
Figure 7:
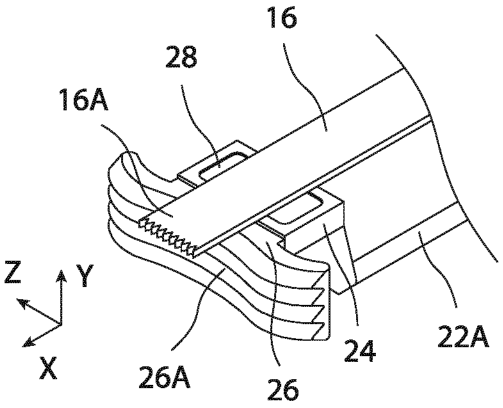

The abutment element 26 aims at abutting against an abutment body part of the patient. This abutment body part may or may not be the patient's anatomical element A to be cut. The abutment element 26 displays a front end 26A and a back end 26B. In the embodiments illustrated on FIGS. 1, 5, 6, 7 and 9, the back end 26B of the abutment element 26 is attached to the blade maintaining element 24. The abutment element 26 can be integrally formed with the blade maintaining element 24, the two elements 24, 26 thus being part of the same piece. In case the patient's abutment body part is a hard body part, as for example a bone, the abutment element 26 may display at least one spike aimed at reversibly securing the cutting guide 18 to it. Preferably, the front end 26A of the abutment element 26 comprises a series of regularly positioned spikes, as can be seen on FIG. 5. In another embodiment shown on FIGS. 6, 7 and 8, the abutment element 26 displays at least one transversal ridge extending along a Z axis, sensibly perpendicular to the elongation axis X and to the Y axis. This ridge aims at reversibly securing the cutting guide 18 to a hard or a soft body part of the patient along the direction of the Y axis. The front end 26A of the abutment element 26 may also display at least one transversal ridge, in order to block the cutting guide movements (and thus the surgical tool 10) movements along the Y axis. Preferably, and as can be seen on FIGS. 6, 7 and 8, the front end 26A of the abutment element 26 displays a series of transversal ridges. Those ridges block the cutting guide 18 along the Y axis and only allow a planar movement aligned with the cutting plan P. Those ridges are shaped to avoid damaging the patient's body parts. The abutment element 26 may have a rounded shape aimed at fitting a natural curve of said body part, as illustrated on FIG. 7. The abutment element 26 thus offers a controlled contact interface between the cutting guide 18 and the patient's anatomical element A to be cut.

During operation, the cooperation of the abutment element 26 and the blade maintaining element 24 enables a huge gain of reliability and strength during the cutting operation: while the blade maintaining element 24 supports and guides the cutting blade 16 relatively to the cutting tool 10, the abutment element 26 rests on an abutment body part and thus guides the cutting tool 10 relatively to the patient's body. This cooperation, thus offers a better stability and a better accuracy in the cutting operation.

Figure 8:
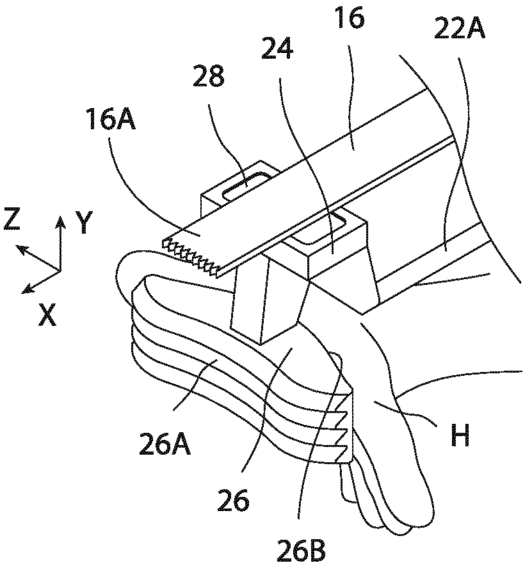

In a further embodiment illustrated on FIG. 8, the back end 26B of the abutment element 26 displays an ergonomic and easy-to-grasp shape. This allows the operator to position their free hand H, meaning the hand which is not holding the handle 14, on the abutment element 26 in a safe and comfortable way, leading to a better haptic feeling during the cutting operation, in particular, a better feeling of any change in the anatomical element A being cut, for example, the transition from the hard cortical tissue to the softer intramedullary inner part of a bone.

As already mentioned, the sliding unit 22 cooperates by sliding with the sliding mechanism 20. The only degree of freedom allowed between the cutting guide 18 and the surgical cutting tool 10 is therefore a translation along the sliding axis X'.

The sliding mechanism 20 is a passive mechanism. This means that the cutting guide 18 is only manually activated by the pressure applied by the operator on the patient's anatomical element A and/or the patient's abutment body part by means of the abutment element 26 during the cutting operation. More precisely, it means that during the cutting operation, the sliding unit 22, the blade maintaining element 24 and the abutment element 26 remain static with regards to the patient's anatomical element A when the cutting guide 18 is activated by the pressure resulting from the surgical cutting tool 10 being pushed towards said patient's anatomical element A.

As can be seen on FIGS. 10 and 3, the sliding mechanism 20 can be, with regards to the casing 12, an external mechanism or an internal mechanism. The sliding mechanism 20 comprises at least one hollow shaft 30, each hollow shaft 30 opening at the front end 12A of the casing 12 and each hollow shaft 30 being configured to receive a sliding rod of the sliding unit 22. In the embodiment illustrated on FIGS. 1 and 2, the sliding mechanism displays two hollow shafts 30, each shaft 30 extending along one flank side 12E of the casing 12. In the embodiment illustrated on FIGS. 3 and 4, the hollow shaft 30 extends along the downside face 12D of the casing 12 and is thus, during the cutting operation, invisible to the operator.

The sliding mechanism 20 enables the cutting guide 18 to display two configurations:

- a resting configuration in which the blade maintaining element 24 the cutting blade 16 nearby the front end 16A of the blade 16,
- an active configuration in which the blade maintaining element 24 cooperates with the cutting blade 16 nearby the back end 16B of the blade 16.

When the cutting guide 18 is activated, meaning when the operator exerts pressure on the cutting tool 10 and the cutting guide 18 against the patient's anatomical element A and/or the patient's abutment body part by the mean of the abutment element 26, the cutting guide 18 changes from its resting configuration to its active configuration.

As can be seen on FIGS. 1 and 2, in some embodiments, the sliding mechanism 20 includes at least one spring element 34. The spring element 34 can be a mechanical spring or, alternatively, a gas spring. Each spring element 34 is embedded at the back end of the sliding mechanism, inside each hollow shaft 30 or bore 32. Each spring element 34 is configured to cooperate with the back end of the sliding unit 22, more precisely each spring element 34 is configured to cooperate with the back end of each sliding rod of the sliding unit 22. This cooperation enables the cutting guide 18 to change from its active configuration into its resting configuration when the cutting guide 18 stops being activated.

As shown in FIGS. 1 to 10, the sliding mechanism 20 and the sliding unit 22 are configured to be positioned below the cutting blade 16 when the surgical cutting tool is in use configuration (i.e., head held by the surgeon for performing a cut). Thanks to this design, the sliding mechanism 20 enables the blade maintaining element 24 to always support the cutting blade 16 close to the patient's anatomical element A. This ensures an optimisation of the stress distribution between the cutting guide 18 and the blade 16 and avoids the buckling of the blade 16, with a minimal obstruction of the view so that the surgeon maintains a clear vision of the blade and the surgical site. The present invention thus reduces the buckling of the blade 16 by giving it an additional support point as close as possible to the patient's anatomical element A.

The invention claimed is:

1. A surgical cutting tool, such as an oscillating saw, comprising:

- a cutting blade aimed at cutting an anatomical element of a patient according to a cutting plane,
- a casing enclosing a motor, said motor being connected to said cutting blade, and a cutting guide comprising:
- a sliding mechanism connected to the casing, wherein the sliding mechanism is a passive mechanism,
- a sliding unit coupled to the casing by means of the sliding mechanism, the sliding unit defining a sliding axis being sensibly parallel with the cutting plane, and cooperates by sliding with the sliding mechanism, the sliding unit being aimed at sliding along the casing,
- a blade maintaining element carried by the sliding unit, the blade maintaining element being configured to cooperate with the cutting blade in order to maintain the cutting blade aligned with the sliding axis,
- an abutment element carried by the sliding unit, said abutment element being aimed at abutting against an abutment body part of the patient,
- wherein the sliding mechanism and the sliding unit are configured to be positioned below the cutting blade in a use configuration, and
- wherein the sliding unit, the blade maintaining element and the abutment element remain static with regards to the patient's anatomical element when the cutting guide is activated by the pressure resulting from the surgical cutting tool being pushed towards said patient's anatomical element.

2. The surgical cutting tool according to claim 1, wherein the cutting blade displays a front and a back end, the front end being the cutting end and the back end being the end connected to the casing, the cutting guide displaying two configurations:

- a resting configuration in which the blade maintaining element cooperates with the cutting blade nearby the front end of the blade,
- an active configuration in which the blade maintaining element cooperates with the cutting blade nearby the back end of the blade,
- wherein the cutting guide changes from the resting configuration to the active configuration when the cutting guide is activated.

3. The surgical cutting tool according to claim 2, wherein the sliding mechanism includes at least one spring element being configured to cooperate with the sliding unit in order to enable the cutting guide to change from the active configuration to the resting configuration when the cutting guide stops being activated.

4. The surgical cutting tool according to claim 1, wherein the blade maintaining element comprises a magnet aimed at cooperating by magnetization with the cutting blade.

5. The surgical cutting tool according to claim 1, wherein the blade maintaining element comprises a slot aimed at receiving the cutting blade.

6. The surgical cutting tool according to claim 1, wherein the abutment element is configured to block the cutting guide along an axis sensibly perpendicular to the sliding axis.

7. The surgical cutting tool according to claim 1, wherein the abutment element displays at least one spike aimed at reversibly securing the cutting guide to an abutment body part of the patient.

8. The surgical cutting tool according to claim 1, wherein the abutment element displays at least one transversal ridge aimed at reversibly securing the cutting guide to an abutment body part of the patient along the direction of the axis sensibly perpendicular to the sliding axis.

9. The surgical cutting tool according to claim 1, wherein the abutment element displays a rounded shape aimed at fitting a natural curve of an abutment body part of the patient.

10. The surgical cutting tool according to claim 1, wherein the abutment element displays an ergonomic shape configured to allow a comfortable and safe positioning of the operator's hand.

11. The surgical cutting tool according to claim 1, wherein the cutting guide is integrally formed with the casing.

12. The surgical cutting tool according to claim 1, wherein the sliding unit is configured to be positioned under the cutting blade.

13. A surgical cutting tool, such as an oscillating saw, comprising:
- a cutting blade aimed at cutting an anatomical element of a patient according to a cutting plane,
- a casing enclosing a motor, said motor being connected to said cutting blade, and a cutting guide comprising:
- a sliding mechanism connected to the casing,
- a sliding unit coupled to the casing by means of the sliding mechanism, the sliding unit defining a sliding axis being sensibly parallel with the cutting plane, and cooperates by sliding with the sliding mechanism, the sliding unit being aimed at sliding along the casing,
- a blade maintaining element carried by the sliding unit, the blade maintaining element being configured to cooperate with the cutting blade in order to maintain the cutting blade aligned with the sliding axis,
- an abutment element carried by the sliding unit, said abutment element being aimed at abutting against an abutment body part of the patient,
- wherein the sliding mechanism and the sliding unit are configured to be positioned below the cutting blade in a use configuration,
- wherein the sliding unit, the blade maintaining element and the abutment element remain static with regards to the patient's anatomical element when the cutting guide is activated by the pressure resulting from the surgical cutting tool being pushed towards said patient's anatomical element, and
- wherein the sliding mechanism includes at least one spring element being configured to cooperate with the sliding unit in order to enable the cutting guide to change from an active configuration to a resting configuration when the cutting guide stops being activated.

14. The surgical cutting tool according to claim 13, wherein the cutting blade displays a front end and a back end, the front end being the cutting end and the back end being an end connected to the casing,
- wherein, in the resting configuration, the blade maintaining element cooperates with the cutting blade nearby the front end of the blade,
- wherein, in the active configuration, the blade maintaining element cooperates with the cutting blade nearby the back end of the blade, and
- wherein the cutting guide changes from the resting configuration to the active configuration when the cutting guide is activated.

15. The surgical cutting tool according to claim 13, wherein the sliding mechanism is a passive mechanism.

16. The surgical cutting tool according to claim 13, wherein the blade maintaining element comprises a magnet aimed at cooperating by magnetization with the cutting blade.

17. The surgical cutting tool according to claim 13, wherein the blade maintaining element comprises a slot aimed at receiving the cutting blade.

18. The surgical cutting tool according to claim 13, wherein the abutment element is configured to block the cutting guide along an axis sensibly perpendicular to the sliding axis.

19. The surgical cutting tool according to claim 13, wherein the abutment element displays at least one spike aimed at reversibly securing the cutting guide to an abutment body part of the patient.

20. The surgical cutting tool according to claim 13, wherein the abutment element displays at least one transversal ridge aimed at reversibly securing the cutting guide to an abutment body part of the patient along the direction of the axis sensibly perpendicular to the sliding axis.

21. The surgical cutting tool according to claim 13, wherein the abutment element displays a rounded shape aimed at fitting a natural curve of an abutment body part of the patient.

22. The surgical cutting tool according to claim 13, wherein the abutment element displays an ergonomic shape configured to allow a comfortable and safe positioning of the operator's hand.

23. The surgical cutting tool according to claim 13, wherein the cutting guide is integrally formed with the casing.

24. The surgical cutting tool according to claim 13, wherein the sliding unit is configured to be positioned under the cutting blade.

* * * * *